United States Patent [19]

Michetti et al.

[11] Patent Number: 5,972,336
[45] Date of Patent: *Oct. 26, 1999

[54] UREASE-BASED VACCINE AGAINST HELICOBACTER INFECTION

[75] Inventors: Pierre Michetti; Andre Blum; Catherine Davin, all of Lausanne, Switzerland; Rainer Haas, Tübingen, Germany; Irène Corthesy-Theulaz, Lausanne, Switzerland; Jean-Pierre Kraehenbuhl, Lausanne, Switzerland; Emilia Saraga, Lausanne, Switzerland

[73] Assignee: OraVax Merieux Co., Cambridge, Mass.

[*] Notice: This patent is subject to a terminal disclaimer.

[21] Appl. No.: 08/085,938

[22] Filed: Jul. 6, 1993

Related U.S. Application Data

[63] Continuation-in-part of application No. 07/970,996, Nov. 3, 1992, abandoned.

[51] Int. Cl.⁶ .......................... A61K 39/02; A61K 9/127; A61K 31/535; A61K 38/00
[52] U.S. Cl. .................................... 424/184.1; 424/234.1; 424/203.1; 424/282.1; 424/94.6; 424/450; 435/7.1; 435/7.9; 435/7.39; 530/323; 514/41; 514/234.5
[58] Field of Search .................... 424/89, 85.8, 234.1, 424/203.1, 282.1, 94.6, 450; 435/7.1, 7.32, 7.9; 530/323; 514/234.5, 41

[56] References Cited

U.S. PATENT DOCUMENTS

| | | | |
|---|---|---|---|
| 4,879,213 | 11/1989 | Fox et al. ...................................... | 435/5 |
| 5,268,276 | 12/1993 | Holmgren et al. ...................... | 435/69.1 |
| 5,538,729 | 7/1996 | Czinn et al. . | |
| 5,679,564 | 10/1997 | Pace et al. . | |
| 5,733,740 | 3/1998 | Cover et al. . | |
| 5,837,240 | 11/1998 | Lee et al. . | |
| 5,843,460 | 12/1998 | Labigne et al. . | |
| 5,859,219 | 1/1999 | Cover et al. . | |

FOREIGN PATENT DOCUMENTS

| | | |
|---|---|---|
| 91310049 | 5/1902 | European Pat. Off. . |
| 0 367 644 | 5/1990 | European Pat. Off. . |
| WO 90/04030 | 4/1990 | WIPO . |
| 9116072 | 10/1991 | WIPO . |
| WO 92/19970 | 11/1992 | WIPO . |
| WO 93/07273 | 4/1993 | WIPO . |
| WO 93/18150 | 9/1993 | WIPO . |
| WO 93/20843 | 10/1993 | WIPO . |

OTHER PUBLICATIONS

Baskerville and Newell, Naturally Occurring Chronic Gastritis and *C pylori* Infection in the Rhesus Monkey: A Potential Model for Gastritis in Man, Gut 29:465–472, 1988.
Parsonnet et al., VIth Int. Workshop of Campylobacter, Helicobacter, and Related Organisms. Oct. 7–10, 1991.
Blaser, Gastric Campylobacter–like Organisms, Gastritis, and Peptic Ulcer Disease, Gastroenterology 93:371–83, 1987.
Bowie et al., Deciphering the Message in Protein Sequences: Tolerance to Amino Acid Substitutions, Science 247:1306–1310, 1990.
Burr et al., Mucosal and Systemic Immunity to *Campylobacter jejuni* in Rabbits after Gastric Inoculation, Infection and Immunity 56:99–105, 1988.
Chamberlain et al., Campylobacter (*Helicobacter*) *pylori* is Peptic Disease a Bacterial Infection? Arch. Intern. Med. 150:951–955, 1990.
Chen et al., Lack of Protection Against Gastric Helicobacter Infection Following Immunisation with Jack Bean Urease: The rejection of a Novel Hypothesis, FEMS Microbiology Letters 116:245–250, 1994.
Chen et al., Immunisation Against Gastric Helicobacter Infection in a Mouse/*Helicobacter felis* Model, The Lancet 339:1120–1121, 1992.
Clayton et al., Molecular Cloning and Expression of *Campylobacter pylori* Species–Specific Antigens in *Escherichia coli* K–12, Infection and Immunity 57:623–629, 1989.
Clayton et al., Nucleotide Sequence of Two Genes from *Helicobacter pylori* Encoding for Urease Subunits, Nucleic Acids Research 18:362, 1990.
Clements et al., Adjuvant Activity of *Escherichia coli* Heat–labile Enterotoxin and Effect on the Induction of Oral Tolerance in Mice to Unrelated Protein Antigens, Vaccine 6:269–277, 1988.
Coelho et al., Duodenal Ulcer and Eradication of *Helicobacter pylori* in a Developing Country, Scandinavian J. Gastroenterology 27:362–366, 1992.
Crabtree et al., Mucosal Humoral Immune Response to *Helicobacter pylori* in Patients with Duodenitis, Digestive Disease and Sciences 36:1266–1273, 1991.
Czinn and Nedrud, Oral Immunization Against *Helicobacter pylori*, Infection and Immunity 59:2359–2363, 1991.
Czinn and Carr, Rapid Diagnosis of *Campylobacter Pyloridis*–associated Gastritis, J. Pediatrics 110:569–570, 1987.
Czinn et al., Protection of Germ–free Mice from Infection by *Helicobacter felis* after Active Oral or Passive IgA Immunization, Vaccine 11:637–642, 1993.
Davin et al., Proceedings of the DDW, American Gastroenterological Association, May 16–19, 1993, 1213, A–304.
Dick–Hegedus and Lee, Use of a Mouse Model to Examine Anti–*Helicobacter pylori* Agents, Scandinavian Journal of Gastroenterology, 26:909–915, 1991.
Donaldson and Toskes, The Relation of Enteric Bacterial Populations to Gastrointestinal Function and Disease, Gastrointestinal Disease, 3rd Edition, (W.B. Saunders Co., Philadelphia 1983) pp. 44–54.
Drazek et al., Characterization and Presumptive Identification of *Helicobacter pylori* Isolates from Rhesus Monkeys, J. Clin. Microbiology 32:1799–1804, 1994.

(List continued on next page.)

*Primary Examiner*—Nita Minnifield
*Attorney, Agent, or Firm*—Clark & Elbing, LLP

[57] ABSTRACT

Method of eliciting in a mammalian host a protective immune response to Helicobacter infection by administering to the host an immunogenically effective amount of a Helicobacter urease or urease subunits as antigen. Vaccine compositions are also provided.

26 Claims, 4 Drawing Sheets

OTHER PUBLICATIONS

Dubois et al., Natural Gastric Infection with *Helicobacter pylori* in Monkeys: A Model for Spiral Bacteria Infection in Humans, Gastroenterology 106:1405–1417, 1994.

Dunn et al., Purification and Characterization of Urease from *Helicobacter pylori*, J. Biol. Chem. 265:9464–9469, 1990.

Eaton et al., Essential Role of Urease in the Pathogenesis of Gastritis Induced by *Helicobacter Pylori* in Gnotobiotic Piglets, Gastroenterology 98:A654, 1990.

Eaton et al., *Campylobacter pylori* Virulence Factors in Gnotobiotic Piglets, Infection and Immunity 57:1119–1125, 1989.

Eldridge et al., Biodegradable Microspheres: Vaccine Delivery System for Oral Immunization, Current Topics in Microbiology and Immunology 146:59–66, 1989.

Elson and Ealding, Generalized Systemic and Mucosal Immunity in Mice After Mucosal Stimulation with Cholera Toxin, J. Immunology 132:2736–2741, 1984.

Elson et al., A Lavage Technique Allowing Repeated Measurement of IgA Antibody in Mouse Intestinal Secretions, J. Immunological Methods 67:101–108, 1984.

Engstrand et al., Inoculation of Barrier–Born Pigs with *Helicobacter pylori*: a Useful Animal Model for Gastritis Type B, Infection and Immunity 58:1763–1768, 1990.

Evans et al., Characterization of the *Helicobacter pylori* Urease and Purification of its Subunits, Microbial. Pathogenesis 10:15–26, 1991.

Ferrero and Labigne, Cloning, Expression and Sequencing of *Helicobacter felis* Urease Genes, Molecular Microbiology 9:323–333, 1993.

Fox et al., *Helicobacter felis* Gastritis in Gnotobiotic Rats: an Animal Model of *Helicobacter pylori* Gastritis, Infection and Immunity 59:785–791, 1991.

Fox et al., *Campylobacter mustelae*, a New Species Resulting from the Elevation of *Campylobacter pylori* subsp. *mustelae* to Species Status, International J. Systemic Bacteriology 39:301–303, 1989.

Fox et al., Gastric Colonization by *Campylobacter pylori* subsp. *mustelae* in Ferrets, Infection and Immunity 56:2994–2996, 1988.

Fox et al., *Helicobacter mustelae*–Associated Gastritis in Ferrets, Gastroenterology 99:352–361, 1990.

Fubara and Freter, Protection Against Enteric Bacterial Infection by Secretory IgA Antibodies, J. Immunology 111:395–403, 1973.

Gilligan and Po et al., Oral Vaccines: Design and Delivery, International Journal of Pharmaceutics 75:1–24, 1991.

Goodwin et al., Transfer of *Campylobacter pylori* and *Campylobacter mustelae* to Helicobacter gen. nov. as . . . *Helicobacter mustelae* comb. nov., Respectively, International J. Systematic Bacteriology 39:397–405, 1989.

Gootz et al., Immunological and Molecular Characterization of *Helicobacter felis* Urease, Infection and Immunity, 62, 793–798, 1994.

Graham, *Campylobacter pylori* and Peptic Ulcer Disease, Gastroenterology 96:615–25, 1989.

Gupta et al., Adjuvants—a Balance Between Toxicity and Adjuvanticity, Vaccine 11:293–306, 1993.

Guruge et al., Detection of Antibodies to *Helicobacter pylori* Cell Surface Antigens, Scand. J. Infect. Dis. 22:457–465, 1990.

Handt et al., *Helicobacter pylori* from the Domestic Cat: Public Health Implications, Infection and Immunity 62:2367–2374, 1994.

Heap and Lee, Immunisation and Gastric Colonisation with *Helicobacter Felis*, Microb. Ecol. Health Dis. 4:S119; VIth International Workshop on Campylobacter, Helicobacter and Related Organisms, Oct. 7–10, 1991.

Holmgren et al., New Cholera Vaccines, Vaccine 7:94–96, 1989.

Hu and Mobley, Purification and N–Terminal Analysis of Urease from *Helicobacter pylori*, Infection and Immunity 58:992–998, 1990.

Hu et al., Purification of Recombinant *Helicobacter pylori* Urease Apoenzyme Encoded by ureA and ureB, Infection and Immunity 60:2657–2666, 1992.

Kazi et al., Cellular and Humoral Immune Responses in *Campylobacter pylori*–associated Chronic Gastritis, J. Pathology 159:231–237, 1989.

Keusch and Bart, Immunization Principles and Vaccine Use, Harrison's Principles of Internal Medicine, 13th Edition vol. 1, pp. 498–511.

Labigne et al., Shuttle Cloning and Nucleotide Sequences of *Helicobacter pylori* Genes Responsible for Urease Activity, J. Bacteriology 173:1920–1931, 1991.

Lee et al., Pathogenicity of *Helicobacter pylori*: A Perspective, Infection and Immunity 61:1601–1610, 1993.

Lee et al., A Small Animal Model of Human *Helicobacter pylori* Active Chronic Gastritis, Gastroenterology 99:131–1323, 1990.

Lee et al., Protection from Helicobacter Infections by Intragastric Immunization with Recombinant Urease, *Helicobacter Pylori*: Basic Mechanisms to Clinical Cure, Poster Abstracts, Nov. 3–6, 1993 (Poster #13).

Lycke and Holmgren, Strong Adjuvant Properties of Cholera Toxin on Gut Mucosal Immune Responses to Orally Presented Antigens, Gastroenterology 59:301–308, 1986.

Mazanec et al., Immunoglobulin A Monoclonal Antibodies Protect Against Sendai Virus, J. Virology 61:2624–2626, 1987.

McGhee et al., The Mucosal Immune System: From Fundamental Concepts to Vaccine Development, Vaccine 10:75–88, 1992.

McSweegan et al., Intestinal Mucus Gel and Secretory Antibody are Barriers to *Campylobacter jejuni* Adherence to INT 407 Cells, Infection and Immunity 55:1431–1435, 1987.

Merrifield, Solid Phase Peptide Synthesis. I. The Synthesis of Tetrapeptide, 85:2149–2154, 1963.

Mestecky, The Common Mucosal Immune System and Current Strategies for Induction of Immune Responses in External Secretions, J. Clin. Immunology 7:265–276, 1987.

Mobley et al., *Helicobacter pylori* Urease: Properties and Role in Pathogenesis, Proceeding of an International Workshop at Deerhurst, Huntsville, Ontario, Canada. Feb. 21–24, 1991. pp. 39–46.

Morris and Nicholson, Ingestion of *Campylobacter pyloridis* Causes Gastritis and Raised Fasting Gastric pH, Am. J. Gastroenterology 82:192–199, 1987.

Nagata et al., Monoclonal Antibodies Against the Native Urease of *Helicobacter pylori*: Synergistic Inhibition of Urease Activity by Monoclonal Antibody Combinations, Infection and Immunity 60:4826–4831, 1992.

Nedrud et al., Combined Oral/Nasal Immunization Protects Mice from Sendai Virus Infection, J. Immunology 139:3484–3492, 1987.

Oderda et al., Eighteen Month Follow Up of *Helicobacter pylori* Positive Children Treated with Amoxycillin and Tinidazole, Gut 33:1328–1330, 1992.

Offit and Clark, Protection Against Rotavirus–Induced Gastroenteritis in a Murine Model by Passively Acquired Gastrointestinal But Not Circulating Antibodies, J. Virology 54:58–64, 1985.

O'Hagan, Intestinal Translocation of Particulates—Implications for Drug and Antigen Delivery, Advanced Drug Delivery Reviews 5:265–285, 1990.

Olivieri et al., Growth of *Helicobacter pylori* in Media Containing Cyclodextrins, J. Clinical Microbiology 31:160–162, 1993.

Orenstein et al., Immunization, Mandell, Douglas and Bennett's Principles and Practice of Infectious Diseases, 4th Ed. (Churchill Livingstone, New York) Part IV, pp. 2770–2790.

Pallen et al., Vaccine against *Helicobacter pylori* Urease, The Lancet 336:186–187, 1990.

Parsonnet et al., *Helicobacter pylori* Infection in Intestinal– and Diffuse–Type Gastric Adenocarcinomas, J. National Cancer Institute 83:640–642, 1991.

Pavlovskis et al., Adjuvant Effect of *Escherichia coli* Heat–labile Enterotoxin on Host Immune Response . . . Campylobacter Antigens, Microb. Ecol. Health Dis. VIth Int. Workshop on Campylobacter . . . Oct. 7–10, 1991.

Peterson, *Helicobacter pylori* and Peptic Ulcer Disease, New England Journal of Medicine 324:1043–1048, 1991.

Rappuoli et al., Development of a Vaccine Against *Helicobacter pylori*: A Short Overview, Eur. J. Gastroenterol. Hepatol. 5/Suppl. 2, 1993.

Rauws et al., *Campylobacter pyloridis*—Associated Chronic Active Antral Gastritis, Gastroenterology 94:33–40, 1988.

Schaedler and Orcutt, Gastrointestinal Microflora, Chapter 14, The Mouse in a Biomedical Research, vol. III (Academic Press, Inc. 1983) pp. 341–345.

Stacey et al., Local and Systemic Antibody Responses During *Helicobacter pylori* Infections, *Helicobacter pylori* and Gastroduodenal Pathology, Pajares et al. (Eds.) (Springer–Verlag, New York, 1993) pp. 165–169.

Stuart et al., Further Studies on Urease Production by Proteus and Related Organisms, J. Bacteriol. 49:437–444, 1945.

Thomas et al., Effect of Oral Immunization with *Helicobacter pylori* Antigens on Colonization by *H. felis* in Mice, Acta Gastro–Enterologica Belgica, VII Int. Workshop on Campylobacter . . . Brussels, Sep. 21–25, 1993.

Von Wulffen, Low Degree of Relatedness Between *Campylobacter pyloridis* and Enteropathogenic Campylobacter . . . by DNA—DNA Blot Hybridization and Immunoblot Studies, FEMS Microbiology Letters 42:129–133, 1987.

Wegmann et al., Gastrospirillum–hominis–assoziierte Gastritis—Eine Zoonose?, Schwetz med. Wschr. 121:245–254, 1991.

Winner III et al., New Model for Analysis of Mucosal Immunity: Intestinal Secretion of Specific Monoclonal . . . Hybridoma Tumors Protects Against *Vibrio cholerae* Infection, Infection and Immunity 59:977–982, 1991.

Wotherspoon et al., Regression of Primary Low–grade B–cell Gastric Lymphoma of Mucosa–associated Lymphoid Tissue Type After Eradication of *Helicobacter pylori*, The Lancet 342:575–577, 1993.

Wyatt et al., Local Immune Response to Gastric Campylobacter in Non–ulcer Dyspepsia, J. Clin. Pathol. 39:863–870, 1986.

Abstracts Submitted for *Helicobacter Pylori*: Beginning the Second Decade and the VIIth Workshop of the European *Helicobacter Pylori* Study Group, Houston, Texas, Sep. 30–Oct. 1, 1994.

Hawtin et al., Investigation of the Structure and Localization of the Urease of *Helicobacter pylori* Using Monoclonal Antibodies, J. General Microbiology 136:1995–2000, 1990.

UREASE-BASED VACCINE AGAINST HELICOBACTER INFECTION

This application is a continuation-in-part of 07/970,996, filed Nov. 3, 1992, now abandoned.

The present invention relates to the prevention and treatment of gastric infection in mammals, including humans. More particularly, the present invention relates to a vaccine suitable for use in the prevention and treatment of Helicobacter infection in mammals, including humans, and to a method of treatment of humans suffering from gastric infection, its consequences such as chronic gastritis or peptic ulcer, and prevention of gastric cancer.

BACKGROUND OF THE INVENTION

Helicobacter infections of human gastric epithelium cause gastritis, are a major factor in the development of peptic ulcers and gastric lymphoma, and may be a risk factor for the development of gastric cancer [1–3]. The most frequent infection agent is *Helicobacter pylori*, followed at a much lower frequency by *Helicobacter heilmanii*. *H. pylori* is a slender S-shaped gram negative microorganism, which is routinely recovered from gastric biopsies of adults and children with histologic evidence of gastritis or peptic ulceration. Evidence for a causal relationship between *H. pylori* and gastroduodenal disease comes from studies in human volunteers, patients with ulcers and gastric cancer, gnotobiotic pigs, and germ-free rodents. Regarding etiology, Koch's postulates were satisfied by creating histologically confirmed gastritis in previously uninfected individuals following consumption of viable microorganisms [4–11], and by treatment to eradicate *H. pylori*, with resolution of the gastritis and, in patients with peptic ulcer disease, a decrease in the recurrence rate [12].

In spite of in vitro susceptibility to many antimicrobial agents, in vivo eradication of established *H. pylori* infections with antimicrobial agents is often difficult to achieve [13]. The microorganism is found within the mucous coat overlying the gastric epithelium and in gastric pits. These are locations which do not appear to allow for adequate antimicrobial levels to be achieved even when antibiotics are given orally at high doses. At the present time, most authorities recommend a "triple therapy", namely a bismuth salt in combination with drugs such as tetracycline and metronidazole for 2–4 weeks. However, the effectiveness of this or other chemotherapeutic regimens remains suboptimal. Furthermore, this treatment may produce serious adverse drug reactions.

At the present time little is known regarding the role of the mucosal immune systems in the stomach. The distribution of immunoglobulin (Ig) producing cells in the normal gastric antrum indicates that IgA plasma cells make up 80% of the total plasma cell population. In addition, the number of plasma IgA cells present in the gastric antrum is comparable to other mucous membranes [14, 15]. A number of studies in humans [16] and in animal models [8,10] have demonstrated specific IgG and IgA responses in serum and in gastric secretions in response to Helicobacter infection. However, the observation that *H. pylori* infection persists as a chronic infection for years, despite inducing a local and systemic immune response, is not encouraging the development of immunization strategies.

Lee et al have reported the ability to infect germ-free rodents with *Helicobacter felis*, a bacterium closely related to *H. pylori*, and reproducibly document histologic gastritis [9, 10]. Since then, this bacterium-host pairing has been accepted as a good model to study Helicobacter-mediated gastritis and its initiating factors [17]. Czinn et al have shown that repetitive oral immunization with a crude lysate of *H. pylori* plus cholera toxin adjuvant induces a vigorous gastrointestinal IgA anti-*H. pylori* response in mice and ferrets [13]. In addition, Chen et al and Czinn et al have recently reported that oral immunization with a crude lysate of *H. felis* induced protection against *H. felis* infection in mice [21, 22]. The exact nature of the antigen(s) responsible for the induction of this protection, however, had not been determined, and no information suggested that the protective antigen(s) of *H. felis* that induced protection against this pathogen would induce a cross-reactive protection extending to another Helicobacter species.

We have demonstrated for the first time that *H. pylori* and *H.felis* share antigenic determinants by obtaining monoclonal antibodies after oral immunization of mice with either *H. pylori* or *H. felis* sonicates and showing that some of these antibodies, directed against *H. pylori*, would crossreact with *H. felis* and vice versa [24;25]. The basis for these cross-reactivities were unknown.

Based on the homology existing between the different known urease amino acid sequences, it has been proposed that urease could be used as a vaccine against *H. pylori* [26]. Nevertheless, despite the homology among the different ureases sequences, cross-reactivity is not the rule. Guo and Liu have shown years ago that ureases of *Proteus mirabilis*, *Proteus vulgaris* and *Providencia rettgeri* show cross-reactivity to each other, while ureases of jack bean and *Morganella morganii* are immunologically distinct from the three former ureases [23]. Even if an antigenic cross-reactivity of *H. pylori* urease with other Helicobacter ureases was a reasonable postulate, no data existed demonstrating that this was really the case until we showed that some *H.felis* monoclonal antibodies crossreacted with *H. pylori* urease [25]. J. Pappo has further demonstrated that mice which have been infected by *H. felis* produce antibodies which crossreact with *H. pylori* urease but not jack bean urease (J. Pappo, unpublished data, 1993).

The use of *H. pylori* urease, or of related ureases, as a vaccine against *H. pylori* infection has previously been proposed by A. Labigne in EPO 367,644 [28]. However, that application contains no evidence of vaccination of any mammal against any Helicobacter infection with urease.

Moreover, while sequence homology with other bacterial ureases might support the use of urease as a vaccine candidate against *H. pylori* infection, the current knowledge of human *H. pylori* infection would certainly not. First, despite the fact that infected individuals often mount a strong antibody response to urease, the anti-urease immune response does not result in clearance or control of the infection. Secondly, *H. pylori* is able to transport urease out of the cell and to shed it from its surface [19, 20]. Thus, urease may not represent an appropriate target for the development of a protective mucosal immune response. Indeed, mucosal immune protection is thought to be mainly mediated by secretory IgA, the agglutinating activity of which would be impaired when the recognized antigen can be shed by the target pathogen and thereby serve as a decoy for the protective antibody. Thirdly, urease appears to be toxic for epithelial cells in culture, and has been suspected to play a role in mucous degradation and in peptic ulceration in vivo. Thus, its use as antigen may be toxic.

Nevertheless, we reasoned that this antigen could be a potentially efficient vaccine if:

first, we would deliver it orally at a sufficiently high dose to elicit a stronger immune response than the naturally occuring one second, the amount of antibodies produced would be high enough to bind all the urease, shed or not shed third, we would use subunits of urease or a molecular species that was non toxic.

In summary, there remains a need for effective treatment and prevention of *H. pylori*-induced gastric infection in humans. Recent data suggested the possibility to generate a vaccine against this infection, but have not provided a clear identification of defined antigen(s), common to all strains of *H. pylori*, that could be incorporated into a safe and effective vaccine.

In this invention, we have identified the urease antigen of *H pylori* as a candidate vaccine and demonstrated its efficacy in an animal model. These results were unexpected in the light of the natural history Helicobacter infections.

SUMMARY OF THE INVENTION

We have discovered that immunity can be induced in mammals susceptible to gastrointestinal Helicobacter infection by exploiting urease epitopes displayed on or about the surface of Helicobacter organisms and using them as a vaccine target. The immunity can be induced by immunization with native urease, but can also be induced with recombinant urease subunit, produced as an enzymatically inactive, therefore non-toxic form. The invention provides a method of inducing immunity to Helicobacter infection by administering to a mucosal surface of a mammal a polyaminoacid preparation, i.e. a mixture of peptides and/or proteins, together with an appropriate adjuvant. This polyaminoacid preparation presents a plurality of epitopes characteristic of and exhibited by a urease enzyme endogenous to the infecting Helicobacter organism. The administration of the polyaminoacid preparation may be performed by the oral route.

The active ingredient of the preparation may comprise natural or biosynthetic epitopes and may take various forms. A non exhaustive list of possible preparations includes purified. naturally occuring or recombinantly produced urease preparations of bacterial or other origin, digests of urease, fusion proteins comprising urease epitopes, truncated forms of urease enzyme, or peptides homologous with the aminoacid sequence of urease. Since development of immunity depends on indution of humoral and/or cellular immune responses which bind to the infecting Helicobacter organism, preferred preparations are those which most closely duplicate the epitopes of the urease endogenous to the infecting organism. For example, preparations displaying the epitopes of urease of *H. pylori* are preferred for administration in humans susceptible to *H. pylori*, and preparations displaying the epitopes of urease of *H. heilmanii* are preferred for the administration in humans susceptible to *H. heilmanii*. However, in accordance with an important aspect of the invention, it has been discovered that urease from other species may be used. For example, we have shown that *H. felis* infection in mice can be prevented by administration of urease from *H. pylori*.

According to one aspect of the invention, there is provided a method of eliciting in a mammalian host a protective immune response to Helicobacter infection wherein an immunologically effective amount of a urease antigen capable of eliciting such a protective immune response, preferably *H. pylori* urease or *H. pylori* urease B subunit, is administered to a mucosal surface of the host.

According to another aspect of the present invention, there is provided a vaccine composition suitable for prevention of Helicobacter infection, comprising an effective amount of a urease antigen, preferably *H. pylori* urease or *H. pylori* urease B subunit, capable of eliciting in a host a protective immune response to Helicobacter infection, in association with a pharmaceutically acceptable carrier or diluent.

According to a further aspect of the present invention, there is provided a method of imparting to a mammalian host passive protection to Helicobacter infection, comprising administering to a mucosal surface of the host an immunologically effective amount of a urease specific antibody produced in a host immunized with a urease, preferably *H. pylori* urease or *H. pylori* urease B subunit, capable of eliciting a protective immune response to Helicobacter infection.

BRIEF DESCRIPTION OF THE DRAWINGS

The invention will now be further described with reference to the accompanying drawings, in which.

DETAILED DESCRIPTION OF THE INVENTION

The present inventors have discovered that oral administration to mice of polyaminoacid preparations exhibiting the epitopes of *H. pylori* urease gives rise to a protective immunological response against *H. felis* in mice, an animal model of generally-accepted value for the study of the immune response to Helicobacter infection [9]. The effect of the protective immune response is that immunized animals, when challenged with pathogen, have a greatly reduced incidence of infection, in comparison to non-immunized animals. Furthermore, the inventors have discovered that oral immunization in mice using *H. pylori* urease B subunit, produced as an enzymatically-inactive recombinant protein, gives rise to a protective immunological response in mice against *H. felis*. The effect of the protective immune response is that immunized animals, when challenged with pathogen, have also a greatly reduced incidence of infection, in comparison to non-immunized animals which do become infected.

Thus, in a first aspect, the present invention provides a method of eliciting in a mammalian host a protective immmune response to Helicobacter infection. The method comprises the step of administering to a mucosal surface of the mammal, including humans, an immunologically effective amount of a urease antigen, preferably *H. pylori* urease, capable of eliciting such a protective immune response.

In a second aspect, the present invention provides a method of eliciting in a mammalian host a protective immune response to Helicobacter infection. The method comprises the step of administering to a mucosal surface of the mammal, including humans, an immunologically effective amount of recombinant, enzymatically inactive, urease B subunit as antigen, preferably recombinant *H. pylori* urease B subunit, capable of eliciting such a protective immune response.

The invention also includes within its scope the treatment or prophylaxis of mammals, including humans, for Helicobacter infection, wherein an immunologically effective amount of a urease, or its subunits, capable of eliciting a protective immune response to Helicobacter infection, is administered to a mucosal surface of a patient. Preferably, the urease is *H. pylori* urease or *H. pylori* urease B subunit, and the urease may be administered either alone or linked to a hydroxylated calcium phosphate, for example hydroxyapatite as a carrier particle. Moreover, it is preferred to administer the *H. pylori* urease in association with a mucosal adjuvant, the B subunit of cholera toxin, muramyl dipeptide or other such adjuvants.

While not being bound by any theory, the present inventors believe that administration of the urease antigen, or B subunit thereof, to a mucosal surface stimulates the common mucosal immune system and perhaps local sites in the gastric mucosa inducing an immune response, including the appearance of *H. pylori* specific IgA antibodies in the gastric secretions, which prevent Helicobacter infection. Since it is a routine matter to conduct pre-clinical trials of candidate vaccines for human use in animal models, it is believed that the methodology of the present invention is effective in humans, especially in the prevention and treatment of peptic ulcers, gastritis, gastric malignancies and other conditions arising as a result of the presence of *H. pylori* and/or *H. heilmanii.*

A—Bacterial Cultures and Urease Purification

The strain of *H. pylori* used in the study originates from a patient with a duodenal ulcer, and has been subcultured on BHI agarose plates to homogeneity. *H. pylori* is cultured in a suitable medium, typically, BHI (Brain-Heart Infusion) medium, containing 0.25% yeast extract and 10% fetal calf serum and supplemented with 0.4% SKIRROW SUPPLEMENT, OXOID 69 Campylobacter selective complement. (SKIRROW™ supplement; OXOID™). The bacteria are incubated overnight under microaerophilic conditions at 37° C. in bottles that are then sealed and shaken at 37° C. for 2 to 3 days to produce a liquid culture. A culture may also be prepared in agarose plates consisting of BHI with 0.25% of yeast extract and 5% of sheep blood under microaerophilic conditions at 37° C. for 3 days. The quantity of bacteria is determined by optical density of the BHI solution at 660 nm, with one optical density unit corresponding to $10^8$ bacteria. Cultures on agarose plates are first resuspended in 154 mM NaCl.

One currently preferred source of polyaminoacid displaying urease epitopes is purified urease, e.g., *H. pylori* urease obtained by following the general method of Dunn et al. J. Biol. Chem. 265, 9464–9469, modified as described below. Following culturing, the *H. pylori* is harvested in water, spun vortexed and spun again to produce a supernatant. The solution containing the urease activity of *H. pylori* (assessed by rapid urease test, see below) is then chromatographed on a SEPHAROSE CL-6B™ (6% bead-formed agarose containing 3,6-anhydro-L-galactose and cross-linked with 2,3-dibromopropanol) sizing column and the fractions which present a strong urease activity are pooled and dialysed overnight and again chromatographed on an anion exchanger gel. The fractions are eluted in increasing NaCl buffer and the collected fractions with a strong urease activity are individually submitted to a SDS gel followed by Coomassie staining. Two distinct bands corresponding to a molecular weight of about 63 and about 28 kDa are identified as urease. The fractions containing urease are pooled to give purified *H. pylori* urease having a purity in the region of 95% to 99%.

B—Oral Immunization with Urease Purified from *H. pylori*

While it is preferred to employ purified *H. pylori* urease obtained as described above as the antigenic material, it will be understood that it is also possible to use, as the antigenic material, any urease or subunit of urease, either naturally occuring or obtained by recombinant DNA techniques, as well as digested fragment thereof, fusion proteins comprising the fragments or the whole urease, truncated urease constructs, or other peptide or protein preparations exhibiting urease epitopes which are capable of eliciting a protective immune response to Helicobacter infection (See below). Thus, it is possible to employ a urease having a substantial homology with respect to *H. pylori* urease and which is effective in raising a cross-protective immune response to Helicobacter. An example of such a urease is jack bean urease, which possesses about 70% homology with *H. pylori* urease. The invention is therefore not limited to the use of intact urease, and covers the use of any polyaminoacid preparation which displays urease epitopes and is effective to generate a protective immunological response in a host to Helicobacter infection. Typically, a urease having a homology of 70–95% homology, for example, 80–90% homology, with respect to *H. pylori* urease, may be employed as the urease antigen in the invention.

A non-limiting list of sources of potentially useful urease preparations includes endogenous urease enzymes of the different Helicobacter species, urease from other bacteria such as *Klebsiella pneumoniae* or *Proteus mirabilis,* and, by analogy, any other urease whith the condition that these ureases share cross-reactive epitopes with *H. pylori* urease. The urease genes of all the organisms mentioned above represent a potential tool for expressing recombinant urease products as a whole protein or as a part thereof.

A non-limiting list of potentially useful urease preparations includes peptides generated from purified urease (the sources are mentioned above), using physical and/or chemical cleavage procedures (i.e. CnBr) and/or proteolytic cleavage (using proteases e.g. V8-protease, trypsin or others); or peptides synthetised chemically and sharing crossreactive epitopes with urease.

Other sources of potentially useful epitopes include epitopes identified by their crossreactivity with urease, as the result of screening with anti-urease antibodies. These peptides can be naturally occuring peptides or peptides resulting from chemical synthesis. Furthermore such peptides can result from the expression of recombinant random oligonucleotides.

Another source of potentially useful epitopes includes epitopes similar to urease as a result of the generation of anti-idiotypic antibodies to urease. Such anti-idiotypic antibodies, generated in any immunocompetent host, are obtained by immunization of this host with anti-urease antibodies, with the goal of generating antibodies directed against anti-urease antibodies, which share structural homologies with urease.

The discussion herein focuses on the use of urease naturally produced by *H. pylori* (section B). However, it will be appreciated that the urease or subunits or constructs thereof mentioned above, capable of eliciting the desired protective immune response, may be produced by recombinant DNA techniques well known in the art. The efficacy of particular preparations may be determined by routine administration using animal models, oral administration of the candidate vaccine, and challenge with pathogen using a protocol substantially similar or identical to the procedure described below.

Tables 1 and 2 below and FIGS. 1–5 describe the results obtained when mice were orally immunized with purified *H. pylori* urease. In this first experiment, administration of the *H. pylori* antigen was carried out by orally administering to the mice *H. pylori* urease purified as described in section A, and coupled to hydroxyapatite crystals, used as a carrier to enhance M cell binding and uptake. Cholera toxin (Sigma) was given as a mucosal adjuvant. In this experiment, groups of female SPF BALB/c six-week old mice were each orally immunized with 30 ug of purified *H. pylori* urease coupled to 1 mg of hydroxyapatite plus 10 ug of cholera toxin adjuvant at day 0, 7, 14 and 21. The mice were then challenged twice with $10^8$ H. felis, at day 28 and 30. For comparison purposes, similar female SPF BALB/c six-week old mice were orally immunized with whole H. pylori lysate (sonicate) and 10 ug cholera toxin at day 0, 7, 14 and 21. The mice were challenged at day 28 and 30 with H. felis. The H. pylori sonicate was prepared by collecting H. pylori from cell cultures, pelleting by centrifugation and resuspending the pellet in 0.9% sodium chloride followed by sonication.

As a control, female SPF BALB/c six-week old mice were orally sham-immunized with 10 ug of cholera toxin and 1 mg of hydroxyapatite at day 0, 7, 14 and 21. The mice were then challenged at day 28 and 30 with H. felis. All mice were housed, immunized, and challenged in parallel. All mice subject to the study were sacrificed on day 35.

C—Oral Immunization with Recombinant Urease Subunits of H. pylori

Genes encoding the structural A and B subunits of H. pylori urease were obtained by polymerase chain reaction (PCR) cloning according to standard procedures, based on previously published sequences [29]. These genes were inserted in a vector (named pEV40) designed for high expression and easy purification of foreign genes in E coli. Briefly, the foreign gene is inserted downstream of a thermo-repressible promoter, and in frame of a sequence encoding for a repeat of six histidines. An ampR gene is present on this vector for selection of transformants. Under the appropriate temperature conditions, the recombinant protein obtained is supplemented by six histidines at the N-terminal, which allow for a one-step affinity purification on a nickel column. Both H. pylori recombinant urease A and B subunits were expressed separately in E. coli, and purified on nickel column to >95% purity.

While it is preferred to employ recombinant H. pylori urease obtained as described above as the antigenic material, it will be understood that it is also possible to use, as the antigenic material, any urease or subunit of urease obtained by recombinant techniques (e.g. fusion protein) expressing antigenic sites of urease, which is capable of eliciting a protective immune response to Helicobacter infection. Thus, it is possible to employ in a construct a urease gene having a substantial homology with respect to H. pylori urease and which is effective in raising a cross-protective immune response to Helicobacter. Examples of such a urease is jack bean urease, which possesses about 70% homology with H. pylori urease, or H. felis urease, which possesses about 88% homology with H. pylori urease. The invention is therefore not limited to the use of H. pylori urease genes and their gene products, and covers the use of any recombinant urease, or the subunits thereof, which is effective to generate a protective immunological response in a host to Helicobacter infection. Typically, a recombinant urease having a homology of 70–95% homology, for example, 80–90% homology, with respect to H. pylori urease, may be employed as the recombinant urease antigen in the invention.

The discussion herein focuses on the use of recombinant H. pylori urease A and B subunits produced by E. coli (section C). However, it will be appreciated that recombinant urease or subunits or constructs thereof mentioned above, capable of eliciting the desired protective immune response, may be produced using other recombinant DNA techniques and other eukaryotic or prokaryotic expression vectors well known in the art.

Tables 3, 4 and 5 below and FIG. 6 describe the results obtained when mice were orally immunized with recombinant H. pylori urease subunits produced in E. coli. In this experiment, administration of the H. pylori antigen was carried out by orally administering to the mice recombinant H. pylori urease A or B subunits produced in E. coli and purified as described above, and coupled to hydroxyapatite crystals, used as a carrier to enhance M cell binding and uptake. Cholera toxin (Sigma) was given as a mucosal adjuvant. In this experiment, groups of female SPF BALB/c six-week old mice were each orally immunized with 30 ug of recombinant H. pylori urease A subunit, coupled to 1 mg of hydroxyapatite plus 10 ug of cholera toxin adjuvant at day 0, 8, 14 and 21. The mice were then challenged twice with $10^8$ H. felis, at day 32, 34 and 36. For comparison purposes, similar female SPF BALB/c six-week old mice were orally immunized with 30 ug of recombinant H. pylori urease B subunit coupled to hydroxyapathite plus 10 ug cholera toxin at day 0, 8, 14 and 21. The mice were challenged three times, at day 32, 34 and 36, with H. felis. As a control, female SPF BALB/c six-week old mice were each orally sham-immunized with 10 ug of cholera toxin and 1 mg of hydroxyapatite at day 0, 8, 14 and 21. The mice were then challenged at day 32, 34 and 36 with H. felis. All mice subject to the study were immunized and challenged in parallel. Animals were sacrificed on day 48 (12 days after challenge) or 10 weeks after challenge.

D—Analysis of Gastric Biopsies, Blood, and Intestinal Secretions

Biopsies were taken from the stomach and blood was obtained from the heart. The intestines were removed and washed with 1 mM PMSF (Boeringher) in PBS buffer to obtain intestinal secretions for ELISA analysis.

To evaluate protection against H. felis colonization, gastric biopsies from each animal were screened for the presence of H. felis by assessing rapid urease activity by the JATROX HP RAPID UREASE test (Rohm Pharma), according to the supplier's directions. Briefly, gastric biopsies are immersed in 0.5 ml supplier's mixture of urea and phenol red, a pH indicator. Urease activity generates ammonia and bicarbonate from urea, and is followed by the colometric change of the solution towards a higher absorbance at 550 nm. Urease activity quantified by spectrophotometric analysis.

Gastric biopsies of each animal included in the experiment described in section B were also cultured on BHI agarose plates, supplemented as above, for the detection of H. felis. After incubation for 3 to 10 days in microaerophilic conditions, the presence of H. felis was confirmed by Gram staining and determination of urease activity. As a very significant correlation was obtained for the detection of H. felis in gastric biopsies between urease tests and H. felis cultures during the first set of experiments (see Table 3), only gastric biopsies urease tests were performed for the detection of H. felis in the experiment described in section C. Detection of H.felis was confirmed by microscopy by two independent investigators, using two different stains (acridine orange and cresyl violet).

Blood samples were allowed to clot for 3 hours at RT, and sera harvested and frozen at −20° C. until analyzed. Intestinal secretions were spun for 5 min. at 4° C. to remove debris, and kept frozen at −20° C. Serum and intestinal samples of each animal were analyzed by ELISA for evaluation of anti-Helicobacter activity, according to standard procedures. Briefly, 96-well plates were coated with a sonicate of H. pylori, followed by saturation with 5% fat-free milk. Samples were serially diluted from 1:1 to 1:1000 and incubated overnight at 4° C. on ELISA plates. Biotinylated anti-mouse IgG (serum) and anti-mouse IgA, followed by streptavidin-Horseradish peroxydase was used for the determination of the antibody levels.

Figure 3:
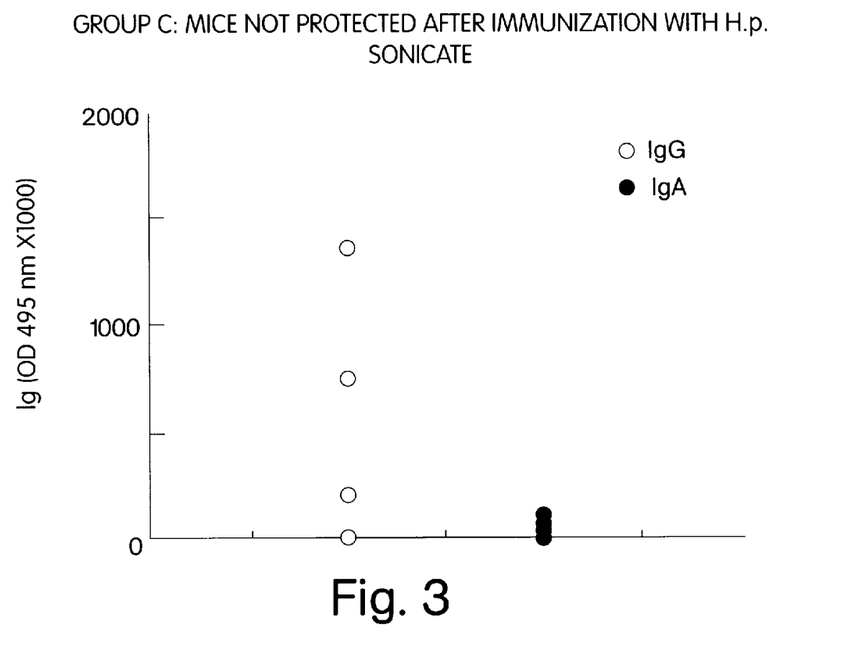
Figure 4:
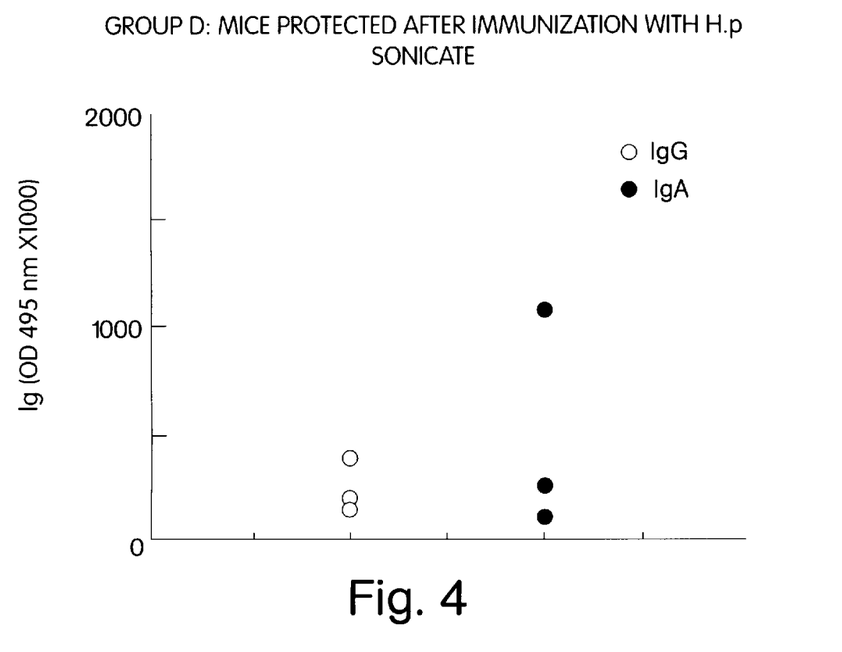
Figure 5:
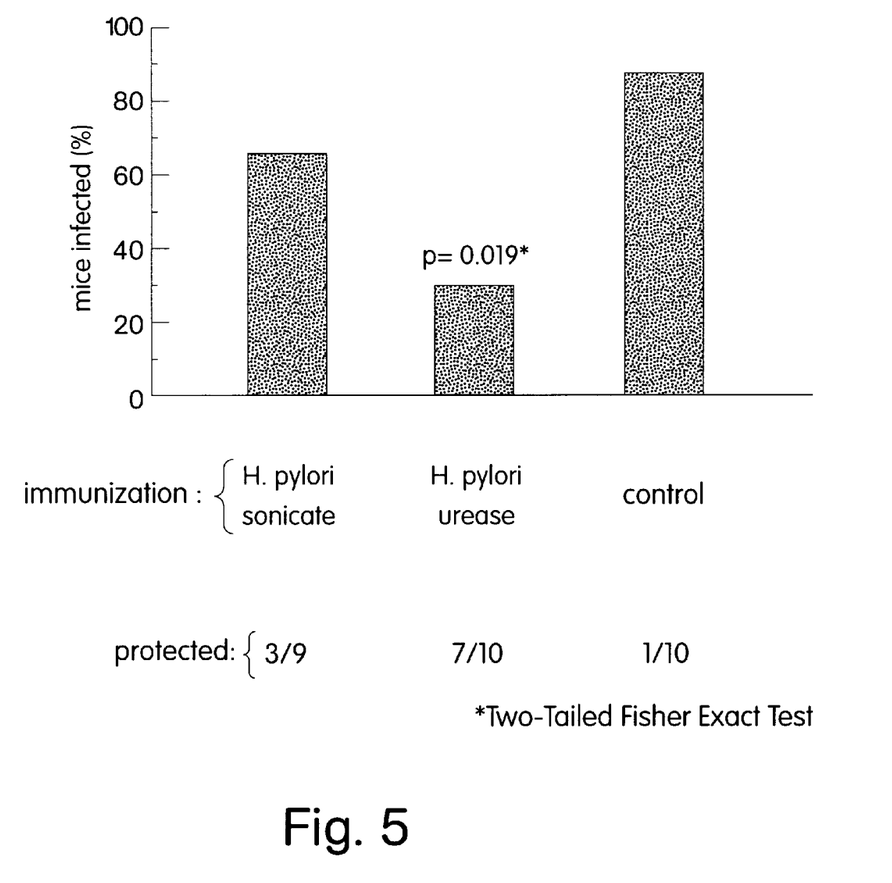
Figure 6A:
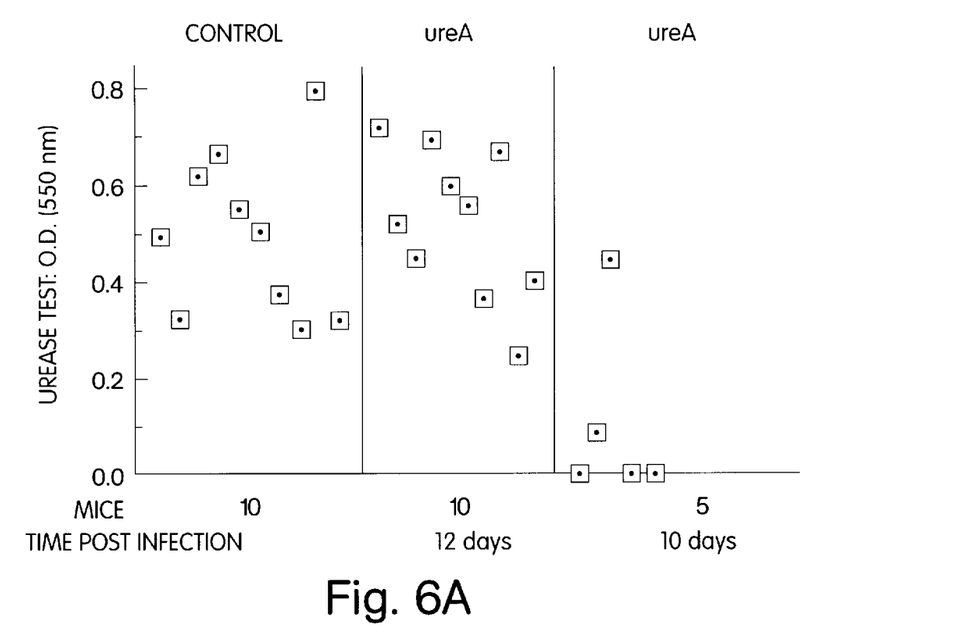
Figure 6B:
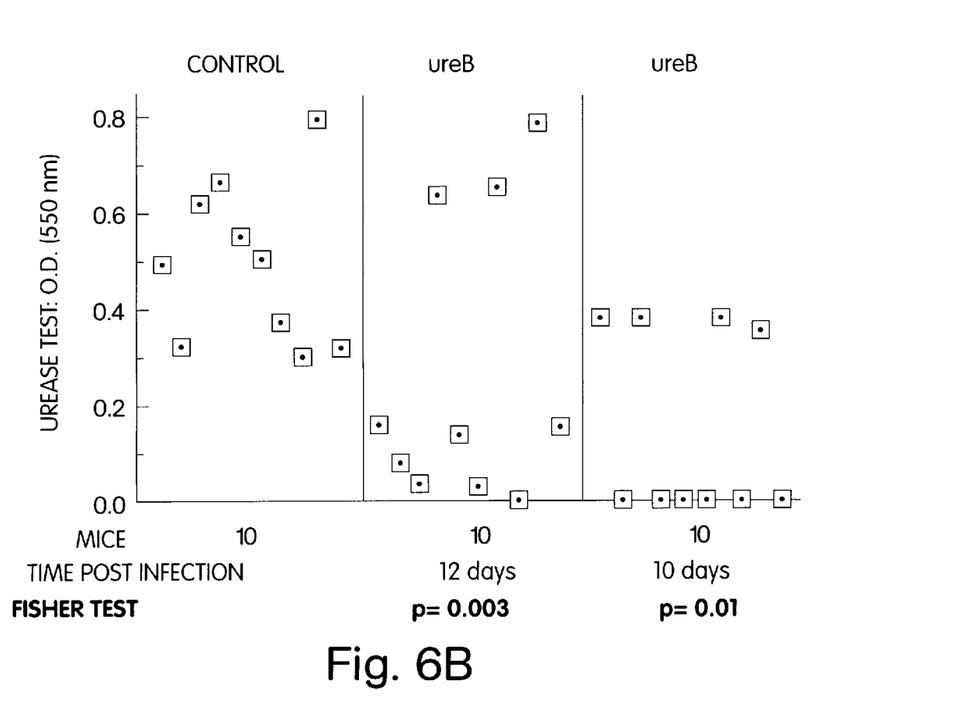

The results of H. felis challenges following immunizations with purified H. pylori urease are set out in Tables 1–3 and FIGS. 1–4 and the results of H. felis challenges following immunizations with recombinant H. pylori urease A and B subunits are set out in Tables 4–6 and FIGS. 5 and 6.

TABLE 1

| mouse number | Immunization | urease test 12h | culture Gram | Immunoglobulins Serum Ig | IgG | Intestinal secretion Ig | IgA |
|---|---|---|---|---|---|---|---|
| 1 | Urease + HF | + | H felis | 27 | 0 | 25 | 258 |
| 2 | Urease + HF | 0 | 0 | 264 | 273 | 221 | 246 |
| 3 | Urease + HF | 0 | 0 | 84 | 44 | 318 | 354 |
| 4 | Urease + HF | + | H felis | 81 | 42 | 12 | 5 |
| 5 | Urease + HF | 0 | 0 | 98 | 137 | 126 | 234 |
| 6 | Urease + HF | + | 0 | 968 | 2093 | 31 | 22 |
| 7 | Urease + HF | 0 | 0 | 98 | 0 | 96 | 34 |
| 8 | Urease + HF | 0 | 0 | 247 | 1010 | 214 | 128 |
| 9 | Urease + HF | 0 | 0 | N.D. | N.D. | 48 | 23 |
| 10 | Urease + HF | 0 | 0 | 50 | 0 | 124 | 99 |
| 11 | Urease | 0 | 0 | 319 | 205 | 44 | 53 |
| 12 | Urease | 0 | 0 | 14 | 0 | 86 | 87 |
| 13 | Urease | 0 | 0 | 0 | 0 | 0 | 0 |
| 14 | Urease | 0 | 0 | 0 | 0 | 43 | 61 |
| 15 | Urease | 0 | 0 | 58 | 0 | 110 | 127 |
| 16 | Urease | 0 | 0 | 140 | 63 | 21 | 37 |
| 17 | Urease | 0 | 0 | 84 | 240 | 114 | 280 |
| 18 | Urease | 0 | 0 | N.D. | N.D. | 93 | 148 |
| 19 | Urease | 0 | 0 | 45 | 0 | 135 | 216 |
| 20 | Urease | 0 | 0 | 261 | 197 | 161 | 261 |
| 21 | CT + HF | 0 | 0 | 0 | 0 | 0 | 2 |
| 22 | CT + HF | + | H felis | 63 | 0 | 310 | 303 |
| 23 | CT + HF | + | H felis | 90 | 0 | N.D. | N.D. |
| 24 | CT + HF | + | H felis | 31 | 0 | 150 | 192 |
| 25 | CT + HF | + | H felis | 197 | 250 | 250 | 440 |
| 26 | CT + HF | + | H felis | 105 | 135 | 214 | 138 |
| 27 | CT + HF | + | H felis | 140 | 47 | 109 | 55 |
| 28 | CT + HF | + | 0 | 0 | 0 | 16 | 15 |
| 29 | CT + HF | + | H felis | 0 | 0 | 0 | 0 |
| 30 | CT + HF | + | H felis | N.D. | N.D. | N.D. | N.D. |
| 31 | HP sonicate + HF | + | H felis | 0 | 0 | 76 | 103 |
| 32 | HP sonicate + HF | + | H felis | 77 | 0 | 11 | 33 |
| 33 | HP sonicate + HF | + | H felis | 549 | 748 | 57 | 36 |
| 34 | HP sonicate + HF | 0 | 0 | 660 | 153 | 180 | 286 |
| 35 | HP sonicate + HF | + | H felis | 730 | 192 | 0 | 5 |
| 36 | HP sonicate + HF | + | H felis | 32 | 0 | 5 | 64 |
| 37 | HP sonicate + HF | 0 | 0 | 400 | 400 | 312 | 1149 |
| 38 | HP sonicate + HF | + | H felis | 1007 | 1360 | 149 | 26 |
| 39 | HP sonicate + HF | 0 | 0 | 220 | 186 | 133 | 122 |
| 40 | HP sonicate | 0 | 0 | 873 | 1016 | 352 | 514 |
| 41 | HP sonicate | 0 | 0 | 727 | 899 | 126 | 191 |
| 42 | HP sonicate | 0 | 0 | 109 | 68 | 44 | 83 |
| 43 | HP sonicate | 0 | 0 | 147 | 949 | 167 | 97 |
| 44 | HP sonicate | 0 | 0 | 845 | 1094 | 246 | 64 |
| 45 | HP sonicate | 0 | 0 | 1217 | 1198 | 210 | 157 |
| 46 | HP sonicate | 0 | 0 | 81 | 0 | 256 | 218 |
| 47 | HP sonicate | 0 | 0 | 329 | 210 | 241 | 276 |
| 48 | HP sonicate | 0 | 0 | 1049 | 737 | 197 | 211 |

In Table 1, which refers to the experiment described in section B, "h" means hour, "Ig" means immunoglobulin, "ND" means "not determined", "urease+HF" means that the mice were immunized with urease (coupled to hydroxyapatite, with cholera toxin) and then challenged with H. felis, "urease" means that the mice were immunized with urease (coupled to hydroxyapatite, with cholera toxin) and not challenged, "CT+HF" means that the mice were sham-immunized with cholera toxin and challenged with H. felis, "HP sonicate+HF" means that the mice were immunized with H. pylori sonicate with cholera toxin and challenged by H. felis, and "HP sonicate" means that the mice were immunized with H. pylori sonicate with cholera toxin and not challenged. In Table 1, the numbers for the antibody results are given as a measure of absorbance at 595 nm multiplied by 1000. The background measured in absence of the antibodies, was subtracted.

The results of experiment described in section B obtained on the basis of the gastric biopsies urease tests and on Gram staining of H. felis cultures are set out in Table 2. Infection was defined by mice with one or more markers of colonization by H. felis, including urease test or Gram staining of cultures.

TABLE 2

| Immunization | Challenge | % infected | % protected |
|---|---|---|---|
| Urease | H. felis | 3/10 (30%) | 7/10 (7.0%)* |
| Sonicate | H. felis | 6/9 (66%) | 3/9 (33%)** |
| CT | H. felis | 9/10 (90%) | 1/10 (10%) |

*p = 0.0198 (two tailed Fisher exact test) compared to CT control
**p = 0.303 (two tailed Fisher exact test) compared to CT control It will be seen from the results set out in Tables 1 and 2 that statistically significant protection against H. felis challenge is obtained with oral immunization using H. pylori urease as compared to that obtained using either H. pylori sonicate or cholera toxin. Referring to Table 2, it will be seen that from a total of 10 immunized animals, only 3 became infected, as compared to 6 of the animals immunized with H. pylori sonicate and 9 of the animals immunized with cholera toxin. Table 2 shows that 70% of the animals were protected from challenge by H. felis as compared to 33% of the animals immunized with H. pylori sonicate and 10% of the animals immunized with cholera toxin and then subjected to H. felis challenge. In other words, 90% of the control mice exposed to H. felis became infected by that pathogen whereas, in contrast, in mice immunized with H. pylori urease 28 days before exposure to H. felis, the infection rate was only 30%. This represents a significant reduction in infection (p=0.0198 in the Fisher exact test, as compared to the control mice). When the mice were orally immunized with H. pylori sonicate, the infection rate was 67% (not significant versus the control). The protection obtained using H. pylori urease is unexpected and could not have been predicted on the basis of the results observed using H. pylori sonicate.

Figure 1:
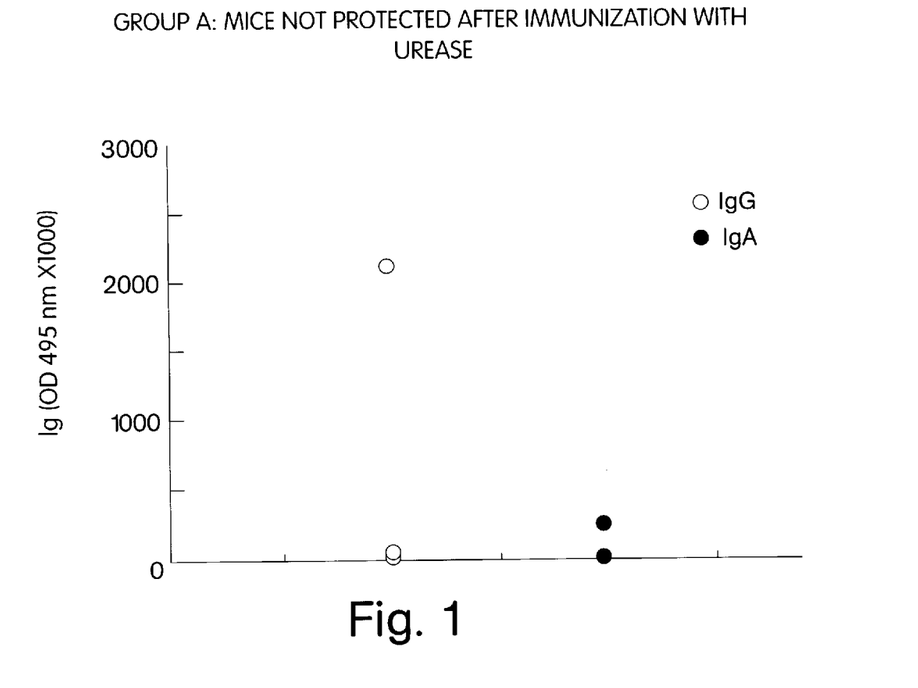
FIGS. 1 through 6 are graphical representations of the results set forth in Tables 1 through 6.
Figure 2:
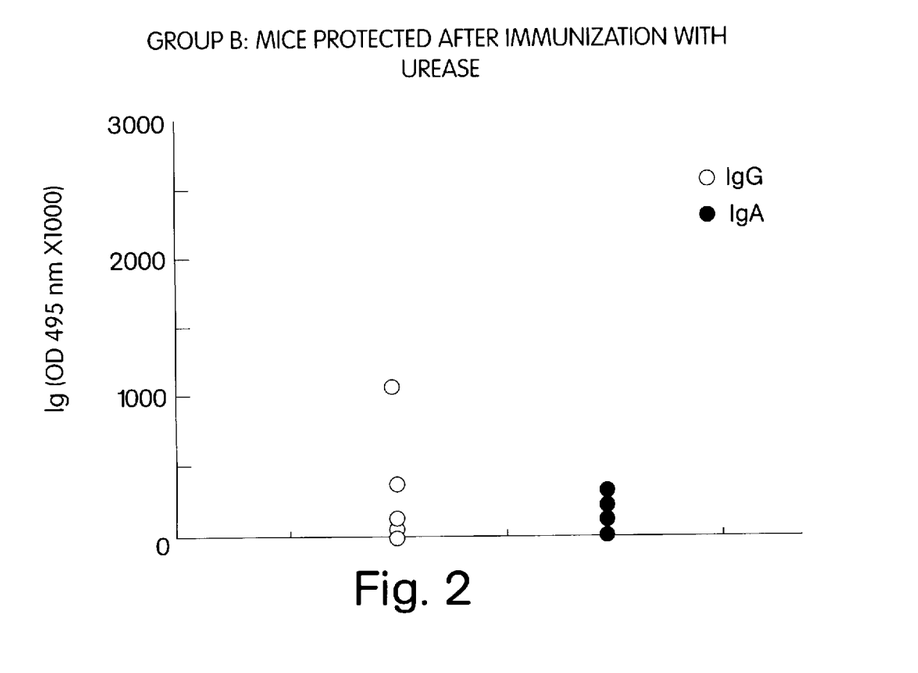

Referring to FIGS. 1–4, FIG. 1 represents graphically the results of tests for antibodies in serum (IgG) and intestinal secretion (IgA) in mice not protected after immunization with urease. These are mice numbers 1, 4 and 6 appearing in Table 1, and constitute Group A. FIG. 2 shows the antibody responses of mice that were protected after immunization with urease (Group B), i.e. mice 2, 3, 5 and 7–10.

FIGS. 3 and 4 relate to the results obtained with mice numbers 31–39. FIG. 3 (Group C) depicts antibody responses of mice not protected after immunization with H. pylori somicate (mice numbers 31, 32, 33, 35, 36 and 38) and FIG. 4 (Group D) depicts the antibody responses of mice protected after immunization with H. pylori sonicate (mice numbers 34, 37 and 39). It is of interest to note with respect to FIGS. 3 and 4 that the IgA antibody responses (but not IgG) are higher in the mice exhibiting protection than in the mice that are not protected, suggesting a correlation between protection and IgA response. Serum IgG responses did not exhibit a correlation. Mucosal IgA but not serum IgG antibodies are known to play a role in protection against bacterial infections of the gut [30].

The results of the correlation between the detection of *H. felis* in gastric biopsies by urease tests and by cultures are set out in Table 3.

TABLE 3

|  | Urease Test + | Urease Test − | Total |
|---|---|---|---|
| *H. felis* culture + | 16 | 0 | 16 |
| *H. felis* culture − | 2 | 30 | 32 |
| Total | 18 | 30 | 48 |

Two-tailed Fishers Exact Test: p < 0.00001

Table 3 shows that a very significant correlation exists between the results of urease tests performed on gastric biopsies and the identification of *H. felis* by cultures. As cultures detected less often *H. felis* infection than urease tests, urease tests were preferred for the diagnosis of *H. felis* infection in mice in the next experiments, due ot its better sensitivity. This approach allowed the duplication of urease tests with larger fragments of the stomach of each mouse, and a further increase in the sensitivity of the urease test. Furthermore, the use of the method with the highest sensitivity prevent an overestimation the protection obtained by the vaccine preparation to be tested. When positive culture is used as the standard for infection, the protection induced after urease immunization during the experiment depicted in section B is as significant as with the combined use of urease test and culture (p=0.021 versus p=0.019).

The results of the experiments described in section C (recombinant urease subunits), obtained on the basis of the gastric biopsies urease tests, are set out in Table 4, 5 and 6 and depicted in FIG. 6.

TABLE 4

| immunization | mice n° | Urease test | Infection |
|---|---|---|---|
| CT | 20 | 0.49 | + |
|  | 21 | 0.31 | + |
|  | 22 | 0.62 | + |
|  | 23 | 0.67 | + |
|  | 24 | 0.55 | + |
|  | 50 | 0.50 | + |
|  | 51 | 0.37 | + |
|  | 52 | 0.29 | + |
|  | 53 | 0.79 | + |
|  | 54 | 0.32 | + |
| ureA + HAP + CT | 40 | 0.67 | + |
|  | 41 | 0.48 | + |
|  | 42 | 0.42 | + |
|  | 43 | 0.65 | + |
|  | 44 | 0.56 | + |
|  | 45 | 0.52 | + |
|  | 46 | 0.33 | + |
|  | 47 | 0.63 | + |
|  | 48 | 0.22 | + |
|  | 49 | 0.37 | + |
| ureB + HAP + CT | 25 | 0.15 | − |
|  | 26 | 0.07 | − |
|  | 27 | 0.03 | − |
|  | 28 | 0.64 | + |
|  | 29 | 0.13 | − |
|  | 30 | 0.02 | − |
|  | 31 | 0.66 | + |
|  | 32 | 0.00 | − |
| ureA + HAP + CT | 68 | 0.00 | − |
|  | 69 | 0.07 | − |
|  | 70 | 0.42 | + |
|  | 71 | 0.00 | − |
|  | 72 | 0.00 | − |
| ureB + HAP + CT | 73 | 0.37 | + |
|  | 74 | 0.00 | − |
|  | 75 | 0.37 | + |

TABLE 4-continued

| immunization | mice n° | Urease test | Infection |
|---|---|---|---|
|  | 76 | 0.00 | − |
|  | 77 | 0.00 | − |
|  | 78 | 0.00 | − |
|  | 79 | 0.39 | + |
|  | 80 | 0.00 | − |
|  | 81 | 0.37 | + |
|  | 82 | 0.00 | − |

In Table 4, "CT" means cholera toxin; "UreA" means recombinant *H. pylori* urease A subunit; "UreB" means recombinant *H. pylori* urease B subunit; and "HAP" means hydroxyapatite crystals. Mice 20 to 54 were sacrificed 12 days post challenge and mice 68 to 82 10 weeks (106 days) post challenge. The results of the urease test performed from biopsies of the stomach of each animal are expressed as OD values at 550 nm. The positive and negative signs depicts the final status of infection of each animal, according to the positivity or negativity of the urease test for detection of *H. felis*. Positivity: $OD_{550}$ values >0.2

TABLE 5

Protection as measured 12 days post challenge

| Immunization | Challenge | % infected | % protected |
|---|---|---|---|
| Urease A subunit | *H. felis* | 10/10 (%) | 0/10 (0%) |
| Urease B subunit | *H. felis* | 3/10 (30%) | 7/10 (70%)* |
| CT | *H. felis* | 10/10 (100%) | 0/10 (0%) | p = 0.0031 (two tailed Fisher exact test) compared to CT control

TABLE 6

Protection as measured 10 weeks post challenge

| Immunization | Challenge | % infected | % protected |
|---|---|---|---|
| Urease A subunit | *H. felis* | 1/5 (20%) | 4/5 (80%)* |
| Urease B subunit | *H. felis* | 4/10 (40%) | 6/10 (60%)** |

*p = 0.003 (two tailed Fisher exact test) compared to CT control
**p = 0.01 (two tailed Fisher exact test) compared to CT control It will be seen from the results set out in Tables 4, 5 and 6 that statistically significant protection against *H. felis* challenge is obtained with oral immunization using recombinant *H. pylori* urease B subunit as compared to that obtained using either recombinant *H. pylori* urease A subunit or cholera toxin. Referring to Table 4, it will be seen that, 12 days post challenge, from a total of 10 immunized animals, only 3 were found infected in the urease B subunit group, as compared to all 10 animals immunized with *H. pylori* A subunit of urease and 10 out of 10 of the animals immunized with cholera toxin. Table 4 shows that 70% of the animals were protected from challenge by *H. felis* as compared to 0% of the animals immunized with *H. pylori* urease A subunit and 0% of the animals immunized with cholera toxin and then subjected to *H. felis* challenge. In other words, 100% of the control mice challenged with *H. felis* became infected whereas, in contrast, in mice immunized with recombinant *H. pylori* urease B subunit the infection rate was only 30%. This represents a significant reduction in infection (p=0.0031, Fisher exact test) as compared to the control mice.

The fact that the protection observed with *H. pylori* urease is entirely conferred by immunization with the B subunit of urease, and that the A subunit has no such effect, was not expected on the basis of our experiment with purified urease. This definition of the roles of the 2 structural subunits of urease in the development of a protective immune response is therefore novel. The protection obtained using recombinant urease B subunit, which is enzymatically inactive also teaches that non toxic forms of urease can be used as oral vaccine against Helicobacter infection. Furthermore these results strongly suggest that recognition of the active site is not required for protection, as an inactive urease B subunit is very unlikely to induce antibodies that will recognize and inhibit the catalytic site of native urease.

Referring to Table 6, it will be seen that, when mice are sacrificed 10 weeks post infection, 60% (6 mice out of 10) of the animals immunized with urease B subunit and 80% (4 mice out 5) of the animals immunized with *H. pylori* urease A subunit were protected against *H. felis* infection. The fact that protection obtained through immunization with urease B subunit lasts over time and that immunization with urease A induces a protection which is delayed compared to the one induced by urease B subunit could not be expected from our experiment with purified urease or with other experiment performed earlier. The fact that urease A subunit immunization confers protection definitively proves that recognition of the active site is not required for protection. FIG. 6 summarizes results obtained after oral immunization with recombinant urease A and B subunits (described in Table 5 and 6)

The present invention also provides vaccine compositions suitable for the prevention of Helicobacter infection. The compositions comprise an effective amount of a urease antigen, preferably *H. pylori* urease or recombinant *H. pylori* urease subunits, capable of eliciting in a host a protective immune response to Helicobacter infection, in association with a pharmaceutically acceptable carrier or diluent.

The vaccines of the invention are administered in amounts readily determined by persons of ordinary skill in this art. Thus, for adults a suitable dosage will be in the range of 10 ug to 100 milligrams, for example 50 ug to 50 mg. Similar dosage ranges will be applicable for children. Carrier systems in humans may include enteric release capsules protecting the antigen from the acidic environment of the stomach, and including urease antigen in a insoluble form as fusion proteins. The vaccine can be administered as a primary prophylactic agent in adults or in children, as a secondary prevention, after successful eradication of *H. pylori* in an infected host, or as a therapeutic agent in the aim to induce an immune response in the host susceptible to contribute to the eradication of *H. pylori*.

As noted above, a suitable mucosal adjuvant is cholera toxin. Others which may be used are muramyl dipeptide or its derivatives, nontoxic derivatives of cholera toxin, including its B subunit, and/or conjugates or genetically engineered fusions of the urease antigen plus cholera toxin or its B subunit. Other suitable delivery methods include biodegradable microcapsules or immune stimulating complexes (ISCOM'S) or liposomes, genetically engineered attenuated live vectors such as viruses or bacteria, and recombinant (chimeric) virus-like particles, e.g. bluetongue. The amount of mucosal adjuvant employed depends on the type of mucosal adjuvant used. For example, when the mucosal adjuvant is cholera toxin, it is suitably used in an amount of 5 ug to 50 ug, for example 10 ug to 35 ug. When used in the form of microcapsules, the amount used will depend on the amount employed in the matrix of the microcapsules to achieve the desired dosage. The determination of this amount is within the skill of a person of ordinary skill in this art.

Suitable carriers for the vaccines of the invention are enteric coated capsules and polylactide-glycolide microspheres. Suitable diluents are 0.2N $NaHCO_3$ and/or saline.

Particulate hydroxylated calcium phosphate (HCP) is especially useful as a carrier for the *H. pylori* urease to be applied to mucosal surfaces. It is believed that the *H. pylori* urease-hydroxylated calcium phosphate conjugate is transported across epithelium where it raises a poly Ig immune response. Preferably, the hydroxylated calcium phosphate is in the form of microparticles suitable for transport across the epithelium, particularly by cells specialized for this purpose (M cells). A preferred form of hydroxylated calcium phosphate is hydroxyapatite, a commercially available crystalline hydroxylated calcium phosphate $Ca_{10}(PO_4)_6(OH)_2$.

Commercially available hydroxyapatite generally consists of slab-like crystals that are chemically and physically analogous to inorganic hydroxyapatite in normal bone tissue. Ingestion of hydroxyapatite should therefore be safe, as evidenced by the existence of nutritional calcium/phosphorus supplements derived from ground bone, which are designed to be ingested. Commercially-high resolution hydroxyapatite (from CalBioChecm) consists of crystals varying widely in size. Crystals over 1 um in length are unlikely to be taken up by M cells. Therefore, for use in the invention, commercial hydroxyapatite crystals are broken into small, relatively uniform crystalline fragments such as by sonication. Preferably, a substantial proportion of the hydroxyapatite is present as fragments of about 0.01–1.0 um. Framentation may be measured either by electron microscopy or light scattering, using standard techniques.

Preferred modes of administration of the *H. pylori* urease antigen are orally, nasally, rectally or ocularly. Oral administration can provide delivery to other G.I. mucosa including the intestinal mucosa.

The vaccines of the present invention may be administered to a mucosal surface in the form of an aerosol, suspension, capsule and/or suppository. The method of administration will be readily apparent to a person of ordinary skill in this art.

The present invention further includes the passive immunization of mammals, including humans, against Helicobacter infection. This is achieved by administering to a mucosal surface of the patient an effective amount of a urease specific antibody. Preferably, an effective amount of a *H. pylori* urease specific IgA monoclonal antibody.

Since the urease of *H. pylori* is shown to represent the antigen involved in inducing protective immunity, a further aspect of the invention is the use of *H. pylori* urease as a diagnostic reagent to measure the immune response of persons who have received a vaccine based on urease or to determine whether an individual is immune or susceptible (and thus in need of vaccination). The present invention also includes the use of urease and urease-specific antibodies to construct assays and kits for diagnosis of Helicobacter immunity, assessment of Helicobacter susceptibility, and definition of immune responses to vaccines.

EXAMPLES

The invention will now be further described by reference to the following non-limiting examples.

a) The Bacterial Strains

*H. felis* was provided by J. Fox (division of Cooperative Medicine, Mass. Institute of Technology, Boston, USA). *H. pylori* was isolated from patients with ulcer disease (CHUV, Lausanne, Switzerland).

b) Bacterial Cultures

Liquid Culture—Bacteria were cultured on BHI (Brain-Heart Infusion, BioMerieux) liquid medium containing 0.25% of yeast extract (Difco) and 10% of fetal calf serum (Inotech) supplemented with 0.4% of Campylobacter selective complement (Oxoid). The bacteria were incubated overnight under microacrophilic conditions at 37° C. and then shaken at 37° C. for 2 to 3 days.

Culture on Agarose plates—The bacteria were cultured on agar plate consisting on BHI with 0.25% of yeast extract and 5% of sheep blood under microacrophiliOuantification 37° C. for 3 days. Quantification—The quantity of bacteria was determined by the optical density of the BHI solution at 660 nm (1 optical density unit corresponding to $10^8$ bacteria).

c) Preparation of Sonicates

*H. pylori* was collected from 31 blood agar plates in 0.15 M NaCl and spun 5 minutes at 1400 g at 4° C. The pellet was resuspended in 3 ml of NaCl and sonicated for 4 minutes. The amount of proteins was evaluated by a Bradford assay (BioRad Kit according to supplier).

d) Coupling of Immunogen to Hydroxyapatite

Immunogen (urease or subunit thereof) was incubated for 1 hour at 4° C. with hydroxyapatite. 1.0 mg of hydroxyapatite was used for 30 ug of immunogen per mouse. At the end of the incubation, 10 μg of cholera toxin was added in a final volume of 200 ul PBS.

Example 1 a) Extraction

*H. pylori* from 30 blood agar plates was harvested in 0.15 M NaCl on ice. The solution was spun 5 minutes at 1400 g at 4° C. The pellet was resuspended in 20 ml of $H_2O$ and vortexed for 45 seconds (maximum speed). The extract was then spun 20 minutes at 6700 g at 4° C. The supernatant was recovered and the quantity of protein was evaluated (see "Quantification" above) and precipitated with 70% of ammonium sulfate.

b) Purification of Urease

The solution was chromatographed on a SEPHAROSE CL-6B™ column (Pharmacia) with PBS (phosphate buffered saline) as mobile phase. The 22 collected fractions which presented a strong urease activity were pooled and dialyzed overnight at 4° C. against 3 liters of PEB (20 mM phosphate buffer, pH 7) and then chromatographed on a Q Sepharose fast flow (Pharmacia) with PEB as mobile phase. The fractions were eluted by 0 to 500 mM NaCl gradient. Ten of the collected fractions with a strong urease activity were individually subjected to an SDS gel followed by a Coomassie staining. The 6 fractions presenting 2 distinct bands corresponding to MW-63 and -28 KDa were pooled and were considered as the purified urease.

Example 2 (See Also Section B)

Mice employed in the immunization studies were lightly anesthetized with ether prior to intragastric immunization. And then, sonicate preparation or purified urease, hydroxyapatite and cholera toxin was suspended in PBS and 200 ul were delivered to the stomach of the respective mice using a polyethylene tubing attached to a hypodermic syringe. This procedure will be referred to as oral immunization.

Three oral immunization protocols were evaluated. These are described below.

Protocol B1—Vaccination with Purified Urease

Female BALB/c six-week old mice (20) were orally immunized with 30 ug of purified of *H. pylori* urease and 1 mg of hydroxyapatite and 10 ug of cholera toxin at day 0, 7, 14 and 21. Ten mice were challenged at day 28 and 30 with $5 \times 10^7$ and $10^8$ *H. felis* from liquid culture.

Protocol B2—Vaccination with Helicobacter Sonicates

Female BALB/c six-week old mice (20) were orally immunized with 2 mg of *H. pylon* sonicate solution at day 0, 7, 14 and 21. Ten mice were challenged at day 28 and 30 with $5 \times 10^7$ and $10^8$ *H. felis*.

Protocol B3—Control

Female BALB/c six-week old mice were orally immunized with 1 mg hydroxyapatite and 10 ug of cholera toxin at day 0, 7, 14 and 21. The mice were challenged at day 28 and 30 with $5 \times 10^7$ and $10^8$ *H. felis*.

At day 35 all mice were sacrificed and biopsies from the stomach were taken as well as intestinal secretions and blood.

Protection and Evaluation

To evaluate protection, biopsies were screened for the urease activity by the JATROX HP rapid urease test (Rohm Pharma) according to the instructions of the supplier. The urease is quantified by a spectrophotometric measurement at 550 nm. The biopsies were also cultured in the presence of *H. felis* and was estimated by Gram staining. Gastric antral biopsies were homogenized and diluted (1:10 and 1:1000) in 0.15 M NaCl and plated onto blood agar plates and incubated under microaerophilic conditions at 37° C. for 4 to 10 days.

Elisa

Intestinal secretions and blood were analyzed by ELISA for the evaluation of antibody titer. The ELISA was carried out as follows. Polystyrene plates (96 wells) were coated with lug/well of purified urease at 37° C. for 2 hrs. Non specific binding sites were blocked with 5% powdered milk in PBS 0.1% TWEEN polyoxyethylenesorbitan at 37° C. for 30 minutes. The plates were washed once with PBS 0.1% TWEEN polyoxyethylenesorbitan. Blood samples were tested at dilution 1:1000 and intestinal secretions 1:1. 100 ul of each sample were added to the antigen coated plates. After 2 hrs of incubation, plates were washed 3 times with PBS 0.1% TWEEN polyoxyethylenesorbitan Anti-mouse biotinylated whole antibody from goat and anti-mouse IgA, IgG and IgM biotinylated (Amersham) were added (100 ul) at dilution 1:500 except for IgA (1:250) and incubated at 37° C. for 1 hr. The plates were washed 3 times with PBS 0.1% TWEEN polyoxyethylenesorbitan and 100 ul of 1:1000 dilution of streptavidin Horseradish peroxidase in PBS 0.1% TWEEN polyoxyethylenesorbitan were added and incubated at 37° C. for 30 minutes. The plates were washed 3 times and 50 ul of 1:50 dilution of o-phenyl-diamine in citrate buffer pH 5.0 with 1 ul/ml of 30% $H_2O_2$ were added and incubated at room temperature for 20 minutes. The absorbance at 495 nm was measured in each well.

Example 3 (See Also Section C)

Mice employed in the immunization studies were lightly anesthetized with ether prior to intragastric immunization. Then, 30 ug recombinant *H. pylori* urease A or B subunit produced in *E. coli* bound hydroxyapatite and supplemented with cholera toxin was suspended in PBS and 200 ul were delivered to the stomach of the respective mice using a polyethylene tubing attached to a hypodermic syringe. This procedure will be referred to as oral immunization.

Three oral immunization protocols were evaluated. These are described below.

Protocol C1—Vaccination with Recombinant Urease A Subunit

Female BALB/c six-week old mice (10) were orally immunized with 30 ug of purified recombinant *H. pylori* urease A subunit and 1 mg of hydroxyapatite and 10 ug of cholera toxin at day 0, 8, 14 and 21. Ten mice were challenged at day 32, 34 and 36 with $10^8$ *H. felis* from liquid culture.

Protocol C2—Vaccination with Recombinant Urease B Subunit

Female BALB/c six-week old mice (10) were orally immunized with 30 ug of recombinant *H. pylori* urease B subunit and 1 mg of hydroxyapatite and 10 ug of cholera toxin at day 0, 8, 14 and 21. Ten mice were challenged at day 32, 34 and 36 with $10^8$ *H. felis* from liquid culture.

Protocol C3—Control

Female BALB/c six-week old mice were orally immunized with 1 mg of hydroxyapatite and 10 ug of cholera toxin at day 0, 8, 14 and 21. The mice were challenged at day 32, 34 and 36 with $10^8$ *H. felis*.

At day 42, or at day 106, mice were sacrificed and multiple biopsies from the stomach were taken.

Protection and Evaluation

To evaluate protection, biopsies of the corpus and antrum of the stomach were screened for urease activity by the JATROX HP rapid urease test (Rohm Pharma) according to the instructions of the supplier. The urease is quantified by a spectrophotometric measurement at 550 nm. The total of corpus and antrum OD values were added to obtain a final OD value for each mouse.

References

1. Blaser, M. J. "Gastric Campylobacter-like organisms, gastritis and peptic ulcer disease" Gastroenterology 1987, 93, 371–383.
2. Graham, D. Y. "*Campylobacter pylori* and peptic ulcer disease" Gastroenterology 1989, i96, 615–625.
3. Parsonnet, J. et al "*Helicobacter pylori* infection in intestinal and diffuse-type gastric adenocarcinomas" J. Natl. Cancer Inst. 1991, 93, 640–643.
4. Marshall, B. J. et al "Attempt to fulfill Koch's postulte for *pyloric* Campylobacter" Med. J. Aust. 1985, 142, 436–439.
5. Morris, A. et al "Ingestion of *Campylobacter pyloridis* causes gastritis and raised fasting gastric pH" Am. J. Gastroenterol. 1987, 82, 192–199.
6. Engstrand, L. et al "Inoculation of barrier-born pigs with *Helicobacter pylori:* a useful animal model for gastritis type B" Infect. Immun. 1990, 53, 1763–1768.
7. Fox, J. G. et al "Gastric colonization by *campylobacter pylori* subsp. mustelae in ferrets" Infect. Immun. 1988, 56, 2994–2996.
8. Fox, J. G. et al "Helicobacter mustelae-associated gastritis in ferrets: an animal model of *Helicobacter pylori* gastritis in humans" Gastroenterology 1990, 99, 352–361.
9. Lee, A. et al "A small animal model of human *Helicobacter pylori* active chronic gastritis" Gastroenterology 1990, 99, 1315–1323.
10. Fox, J. G. et al "Helicobacter felis gastritis in gnotobiotic rats: an animal model of *Helicobacter pylori* gastritis" Infect. Immun. 1991, 59, 785–791.
11. Eaton, K. A. et al "*Campylobacter pylori* virulence factors in gnotobiotic piglets" Infect. Immun. 1989, 57, 1119–1125.
12. Peterson, W. L. "*Helicobacter pylori* and peptic ulcer disease" N. Engl. J. Med. 1991, 324, 1043–1048.
13. Czinn, S. J. and Nedrud, J. G. "Oral immunization against *Helicobacter pylori*" Infect. Immun. 1991, 59, 2359–2363.
14. Brandtzaeg, P. "Role of H chain and secretory component in receptor-mediated glandular and hepatic transport of immunoglobulins in man" Scand. J. Immunol. 1985, 22, 111–146.
15. Brandtzaeg, P. et al "Production and secretion of immunoglobulins in the gastrointestinal tract" Ann. Allergy 1987, 59, 21–39.
16. Wyatt, J. I. et al "Local immune response to gastric campylobacter in non-ulcer dyspepsia" J. Clin. Path. 1986, 39, 863–870.
17. Lee, A. et al. "Pathogenicity of *Helicobacter pylori:* A Perspective" Infect. Immun. 1993, 61, 1601–1610.
18. Pallen, M. J. and Clayton, C. L. "Vaccination against *Helicobacter pylori* urease, letter" Lancet, 1990, 336, 186.
19. Evans, D. J. et al. "Urease-associated heat shock protein of *Helicobacter pylori*" Infect. Immun. 1992, 60, 2125–2127.
20. Ferrero, R. L. and Lee, A. "The importance of urease in acid protection for the gastric-colonising bacteria *Helicobacter pylori* and Helicobacter felis sp. nov." Microb. Ecol. Health Dis. 1991, 4, 121–134.
21. Chen, et al. "Immunization against gastric Helicobacter infection in a mouse/Helicobacter felis model, letter" Lancet, 1992, 339,1120–1121.
22. Czinn, S. et al. "Oral immunization protects germ-free mice against infection from *Helicobacter felis*". Proceedings of the DDW, American Gastroenterological Association. May 10–13, 1992, 1321, A-331.
23. Guo, M. and Liu, P. V. "Serological specificities of ureases of Proteus species". J. Gen. Microbiol, 1965, 136, 1995–2000.
24. Michetti, P. et al. "Specificity of mucosal IgA response in Balb/C mice following *H.felis* or *H. pylori* challenges. Proceedings of the DDW, American Gastroenterological Association. May 10–13, 1992, 1001, A-251.
25. Davin, C. et al. "H.pylori urease elicits protection against *H.felis* infection in mice". Proceedings of the DDW, American Gastroenterological Association. May 16–19, 1993, 1213, A-304.
26. Pallen, M. J. and Clayton, C. L. "Vaccination against *Helicobacter pylori* urease". Lancet 1990, 336, 186-7.
27. Pimentel, J. L. and Cook, M. E. "Improved growth in the progeny of hens immunised with jackbean urease". Poultry Sci. 1988, 64, 434–439.
28. Labigne, A. "Sequences of nucleotides coding for a protein having an urease activity". EPO patent application # EP O 367 644 A1, 1989. International publication # WO 90/04030, 1990.
29. Clayton, C. L. et al. S. "Nuleotide sequence of two genes from *Helicobacter pylori* encoding for urease subunits". Nucleic Acid Res. 1990, 18, 362.
30. McGhee, J. R and Kyono, H. "New perspectives in vaccine development: mucosal immunity to infections". Infect Agents Dis. 1993, 2, 55–73.

We claim:

1. A method of eliciting a protective immune response to Helicobacter infection in a mammal, said method comprising administering to a mucosal surface of said mammal an immunogenically effective amount of a purified, recombinant, enzymatically inactive polypeptide comprising the sequence of an A subunit of a naturally occurring Helicobacter urease to elicit said protective immune response to Helicobacter infection in said mammal.

2. The method of claim 1, wherein said mucosal surface is oral.

3. The method of claim 1, wherein said polypeptide is produced as a fusion protein.

4. The method of claim 3, wherein said fusion protein comprises a cholera toxin subunit.

5. The method of claim 1, wherein said polypeptide is administered in association with a mucosal adjuvant.

6. The method of claim 5, wherein said mucosal adjuvant is cholera toxin.

7. The method of claim 1, wherein said mammal is human.

8. The method of claim 1, wherein said polypeptide is administered in association with a hydroxylated calcium phosphate.

9. The method of claim 8, wherein said hydroxylated calcium phosphate is hydroxyapatite.

10. The method of claim 9, wherein said hydroxyapatite is in the form of particles suitable for transport across epithelium.

11. A method of eliciting a protective immune response to Helicobacter infection in a mammal, said method comprising administering to a mucosal surface of said mammal an immunogenically effective amount of a purified, recombinant, enzymatically inactive polypeptide comprising the sequence of a B subunit of a naturally occurring Helicobacter urease to elicit said protective immune response to Helicobacter infection in said mammal.

12. The method of claim 11, wherein said mucosal surface is oral.

13. The method of claim 11, wherein said polypeptide is produced as a fusion protein.

14. The method of claim 13, wherein said fusion protein comprises a cholera toxin subunit.

15. The method of claim 11, wherein said polypeptide is administered in association with a mucosal adjuvant.

16. The method of claim 15, wherein said mucosal adjuvant is cholera toxin.

17. The method of claim 11, wherein said mammal is human.

18. The method of claim 11, wherein said polypeptide is administered in association with a hydroxylated calcium phosphate.

19. The method of claim 18, wherein said hydroxylated calcium phosphate is hydroxyapatite.

20. The method of claim 19, wherein said hydroxyapatite is in the form of particles suitable for transport across epithelium.

21. A vaccine for administration to a mucosal surface of a mammal for inducing a protective immune response to Helicobacter infection in said mammal, the vaccine comprising (i) a purified, recombinant, enzymatically inactive polypeptide comprising the sequence of an A subunit of a naturally occurring Helicobacter urease, and (ii) a mucosal adjuvant, disposed in a pharmaceutically acceptable carrier or diluent.

22. A vaccine for administration to a mucosal surface of a mammal for inducing a protective immune response to Helicobacter infection in said mammal, the vaccine comprising (i) a purified, recombinant, enzymatically inactive polypeptide comprising the sequence of a B subunit of a naturally occurring Helicobacter urease, and (ii) a mucosal adjuvant, disposed in a pharmaceutically acceptable carrier or diluent.

23. The method of claim 1, wherein said naturally occurring Helicobacter urease is from *Helicobacter pylori*.

24. The method of claim 11, wherein said naturally occurring Helicobacter urease is from *Helicobacter pylori*.

25. The vaccine of claim 21, wherein said naturally occurring Helicobacter urease is from *Helicobacter pylori*.

26. The vaccine of claim 22, wherein said naturally occurring Helicobacter urease is from *Helicobacter pylori*.

* * * * *